(12) United States Patent
Frederiksen et al.

(10) Patent No.: US 11,999,928 B2
(45) Date of Patent: Jun. 4, 2024

(54) BREWING METHOD

(71) Applicant: Novozymes A/S, Bagsvaerd (DK)

(72) Inventors: Anne Mette Bhatia Frederiksen, Copenhagen (DK); Lars Beier, Lyngby (DK); Stefan Kreisz, Copenhagen (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 17/684,693

(22) Filed: Mar. 2, 2022

(65) Prior Publication Data

US 2022/0380707 A1     Dec. 1, 2022

Related U.S. Application Data

(63) Continuation of application No. 13/509,056, filed as application No. PCT/EP2010/067297 on Nov. 11, 2010, now abandoned.

(60) Provisional application No. 61/261,404, filed on Nov. 16, 2009.

(30) Foreign Application Priority Data

Nov. 13, 2009  (EP) ..................................... 09175967

(51) Int. Cl.
| C12C 5/00 | (2006.01) |
| C12C 7/047 | (2006.01) |
| C12N 9/28 | (2006.01) |
| C12N 9/44 | (2006.01) |

(52) U.S. Cl.
CPC .............. *C12C 5/004* (2013.01); *C12C 7/047* (2013.01); *C12N 9/2417* (2013.01); *C12N 9/2457* (2013.01); *C12Y 302/01041* (2013.01)

(58) Field of Classification Search
CPC ......... C11B 1/108; C11B 13/00; C11B 3/003; C11B 1/10; C11B 1/025; C12P 7/64; C12P 7/10; C12N 9/2417; C12N 9/58; C12N 9/2428; C12N 9/52; C12N 9/50
See application file for complete search history.

(56) References Cited

U.S. PATENT DOCUMENTS

| 4,355,047 A | 10/1982 | Line |
| 5,082,781 A | 1/1992 | Yamagata |
| 5,312,739 A | 5/1994 | Shaw |
| 5,356,808 A | 10/1994 | Purdue |
| 6,162,628 A | 12/2000 | Cherry |
| 2008/0003341 A1 | 1/2008 | Beier |
| 2008/0279980 A1 | 11/2008 | Bisgard-Frantzen |

FOREIGN PATENT DOCUMENTS

| EP | 0083991 A2 | 7/1983 |
| EP | 0242075 A1 | 10/1987 |
| EP | 0839916 A1 | 5/1998 |
| WO | 1988/003556 A1 | 5/1988 |
| WO | 1999/27124 A1 | 6/1999 |
| WO | 2002074895 A2 | 9/2002 |
| WO | 2004011591 A1 | 2/2004 |
| WO | 2005/113785 A2 | 12/2005 |
| WO | 2005121305 A1 | 12/2005 |
| WO | 2007113292 A2 | 10/2007 |
| WO | 2007144393 A1 | 12/2007 |
| WO | WO-2008148845 A2 * | 12/2008 ............. A21D 8/042 |
| WO | 2009074650 A2 | 6/2009 |
| WO | 2009075682 A1 | 6/2009 |

OTHER PUBLICATIONS

Ahokas et al, 1990, Genetica, vol. 82, No. 2, pp. 73-78.
Ahokas et al, 1990, J Inst Brew, vol. 96, No. 1, pp. 27-31.
Enevoldsen, 1970, J Inst Brew, vol. 76, No. 6, pp. 546-552.
Enevoldsen, 1978, J Jap Soc Starch Sci, vol. 25, No. 2, pp. 89-99.
Evans et al., 2003, J. Am. Soc. Brew. Chem. vol. 61, pp. 210-218.
He and Hu Shipin Kexue, 2010, vol. 31, pp. 236-239.
Linko et al., Annals New York Academy of Sciences, 1983, vol. 413, pp. 352-354.
Noonan GJ, Brewing Lager Beer, Chapter 7 Enzymes, 1996.
Noonan, 1986, New Brewing Lager Beer.
Outtrup and Norman, Starch, vol. 36, pp. 405-441, 1984.
Tegge et al, 1986, Starch, vol. 38, No. 2, pp. 61-67.
Tegge et al, 1986, Starch, vol. 38, No. 2, pp. 61-67—English Translation.
Elvig et al, WO 2007-113292 A2 Sequences (2007).
Elvig et al, WO 2009-075682 A1 Sequences (2009).

* cited by examiner

*Primary Examiner* — Vera Stulii
(74) *Attorney, Agent, or Firm* — Yoshimi D. Barron

(57) ABSTRACT

A method of mashing comprising providing a grist comprising malt and adjunct; and contacting the grist with a pullulanase; an alpha amylase; and a maltogenic alpha amylase and/or a beta amylase to make a wort. An enzyme composition comprising a pullulanase; an alpha amylase; and a maltogenic alpha amylase and/or a beta amylase and the use of these enzymes in brewing is disclosed.

12 Claims, No Drawings
Specification includes a Sequence Listing.

BREWING METHOD

CROSS-REFERENCE TO RELATED APPLICATIONS

This application is a continuation of U.S. application Ser. No. 13/509,056 filed on May 10, 2012 which is a 35 U.S.C. 371 national application of PCT/EP2010/067297 filed Nov. 11, 2010, which claims priority or the benefit under 35 U.S.C. 119 of European application no. 09175967.0 filed Nov. 13, 2009 and U.S. provisional application No. 61/261,404 filed on Nov. 16, 2009, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

This invention relates to brewing. It relates to the use of a combination of a pullulanase, an alpha amylase and a maltogenic alpha amylase and/or a beta amylase for brewing. It also relates to the use of a sucrose tolerant maltogenic alpha amylase for brewing.

BACKGROUND OF THE INVENTION

Brewing processes are well known in the art. It involves the steps of malting, mashing and fermentation/maturation. Briefly; during malting, grains are allowed to germinate and then dried and optionally roasted. The malting process causes the activation of a number of enzymes in the grain which can convert the starch in the grain to sugar. Prior to mashing, the malt is crushed to form grist, which is mixed with water to form a mash and then sent for mashing. Mashing is the process of converting starch in the mash into fermentable and un-fermentable sugars. The mashing process is conducted over a period of time at various temperatures in order to activate the endogenous enzymes responsible for the degradation of proteins and carbohydrates. Exogenous enzymes may also added during the mashing process to speed up the reactions and enable better control over the brewing process. Towards end of mashing, the temperature may be raised to about 75° C. (165-170° F.) (known as a mashing-off). After the mashing, the resulting liquid is strained from the grains in a process known as lautering. The liquid resulting from lautering is known as wort. The wort which is rich in sugars is then boiled with hops, cooled and then fermented to ethanol using yeast. The resulting beer is conditioned for a week to several months and then packaged.

Though traditionally beer has been brewed from just barley malt, hops and water; malt is an expensive raw material because it requires superior quality grains, water for germination and energy for kilning/roasting. Traditionally around 25-30% of unmalted grains, also called adjuncts, such as maize, rice, sorghum, and wheat, refined starch or readily fermentable carbohydrates such as sugar or syrups are also included in the grist. Adjuncts are used mainly because they are readily available and provide carbohydrates at a lower cost than is available from barley malt. Other advantages may also be achieved, e.g. enhanced physical stability, superior chill-proof qualities, and greater brilliancy. However when adjuncts with higher gelatinization temperatures, for example, maize or rice are used, they must be cooked and gelatinized in a separate "cereal cooker" before being mixed into the malt mash ahead of saccharification. Thus, while the use of adjunct reduces the costs of raw material price, it requires an additional investment in the cereal cooker as well as an additional cost for energy for heating the adjunct. These additional expense requirements have discouraged brewers from increasing the adjunct ratio and also use different adjuncts of choice in their brewing process.

Of late, there is a dramatic changing in raw material prices caused by increased demand for grains, global water shortage, changing weather patterns etc. This has forced the brewing industry to focus on production efficiency as well as raw material savings.

There exists a need for improved processes in brewing which will bring down costs and/or increase production efficiency.

SUMMARY OF THE INVENTION

The inventors have surprisingly found that a combination of a pullulanase, an alpha amylase and either a maltogenic alpha amylase or a beta amylase or both can result in improved production efficiencies. It facilitates the inclusion of a greater percentage of adjuncts during brewing; improves saccharification profile and also results in a beer that is substantially similar to a beer brewed in a traditional way.

The inventors have also surprisingly found that when such a combination is used, there is increased energy savings because the processes can be done at a lower temperature and the cereal cooking can be dispensed with.

The inventors have also surprisingly found that there is increased production efficiency and lower costs when the maltogenic alpha amylase is also sucrose tolerant.

Thus in one aspect, the invention relates to a method of mashing comprising:
  a) providing a grist comprising malt and adjunct; and
  b) contacting the grist with
    i) a pullulanase;
    ii) an alpha amylase; and
    iii) a maltogenic alpha amylase and/or a beta amylase
  to make a wort.

In one aspect, the wort is converted into beer.

In another aspect, the invention relates to the use of a sucrose tolerant maltogenic alpha amylase in brewing.

In one aspect, the invention relates to the use of a pullulanase, an alpha amylase and a maltogenic alpha amylase and/or a beta amylase in brewing.

In another aspect, the invention relates to an enzyme composition comprising a pullulanase; an alpha amylase; and a maltogenic alpha amylase and/or a beta amylase.

In one aspect, the maltogenic amylase is a maltogenic amylase having at least 70% identity to SEQ ID NO 1.

In another aspect, the alpha amylase has at least 70% identity to SEQ ID No 2.

In one aspect, the pullulanase has at least 70% identity to SEQ ID No 3.

In one aspect, the beta amylase has at least 70% identity to SEQ ID No 4.

In another aspect, the maltogenic amylase has at least 10% more sucrose tolerance than the amylase denoted in SEQ ID NO 1.

In yet another aspect, the maltogenic amylase has at least 10% more thermo stability than the amylase denoted in SEQ ID NO 1.

In one aspect, the maltogenic amylase has substitutions at specific positions when compared to the amylase denoted in SEQ ID NO 1.

In one aspect, the pullulanase is thermostable.

In another aspect, the beta amylase is thermostable.

In one aspect, the grist comprises 30-80% malt and 30-80% adjunct.

In another aspect, the adjunct includes adjuncts which have a gelatinization temperature higher than malt starch, for example, but not limited to maize and rice.

DETAILED DESCRIPTION OF THE INVENTION

In one aspect, the invention relates to a method of mashing comprising:
a) providing a grist comprising malt and adjunct; and
b) contacting the grist with
  i) a pullulanase;
  ii) an alpha amylase; and
  iii) a maltogenic alpha amylase and/or a beta amylase to make a wort.

The term "grist" is understood as the starch or sugar containing material that is the basis for beer production, for example, but not limited to barley malt and the adjunct.

The term "malt" is understood as any malted cereal grain, in particular, barley.

The term "starch gelatinization" is understood as the irreversible order-disorder transition that starch undergoes when heated in the presence of water. Differential Scanning calorimetry (DSC) in one technique that can be employed to study the gradual process of starch gelatinization describing the onset and peak temperature ($T_o$ & $T_p$) of starch gelatinization.

The term "onset gelatinization temperature ($T_o$)" is understood as the temperature at which the gelatinization begins.

The term "peak gelatinization temperature ($T_p$)" is understood as the temperature at endotherm peak.

The term "conclusion gelatinization temperature ($T_c$)" is understood as the temperature at which the gelatinization has terminated.

The term "adjunct" is understood as that part of the grist which is not malt. The adjunct may be any starch rich plant material such as, but not limited to, maize, rice, sorghum, and wheat. Preferred adjuncts for the invention include adjuncts where the starch has a higher onset, peak, and conclusion gelatinization temperature ($T_o$, $T_p$, $T_c$) than barley or malt, more preferably above 5° C. higher than malt starch. The adjuncts can be gelatinized prior to mashing or they can be added as such to the grist.

In one aspect, the adjuncts are not gelatinized prior to mashing.

The term "mash" is understood as a starch containing slurry of the grist comprising crushed barley malt, crushed unmalted grain, other starch containing material, or a combination thereof, steeped in water to make wort. "Mashing" is the process of converting starch in the mash into fermentable and un-fermentable sugars The term "wort" is understood as the unfermented liquor run-off following extracting the grist during mashing.

A "maltogenic alpha amylase" is understood as an enzyme classified in EC 3.2.1.133. The enzymatic activity does not require a non-reducing end on the substrate and the primary enzymatic activity results in the degradation of amylopectin and amylose to maltose and longer maltodextrins. It is able to hydrolyze amylose and amylopectin to maltose in the alpha-configuration.

As used herein the term "sucrose tolerance" is understood as the % residual alpha-amylase activity of an enzyme incubated for 15 min at 60° C. in a buffer system (pH 5.0) comprising 10% sucrose. 100% sucrose tolerance is defined as the residual alpha-amylase activity of an enzyme obtained when no sucrose is added to the buffer system.

Conventional machinery, equipments and materials can be used during mashing. The grist is mixed with water prior to mashing. The water may preferably, before being added to the grist, be preheated in order for the mash to attain the desired mash temperature at the moment of mash forming. If the temperature of the formed mash is below the desired mashing temperature additional heat is preferably supplied in order to attain the desired process temperature. Preferably, the desired mashing temperature is attained within 15 minutes, or more preferably within 10 minutes, such as within 9, 8, 7, 6, 5, 4, 3, 2 minutes or even more preferably within 1 minute after the mash forming, or most preferably the desired mashing temperature is attained at the mash forming. The temperature profile of the mashing process may be a profile from a conventional mashing process wherein the temperatures are set to achieve optimal degradation of the grist dry matter by the malt enzymes.

The malt is preferably derived from one or more of the grains selected from the list comprising maize, barley, wheat, rye, sorghum, millet and rice. Preferably, the malt is barley malt.

The grist preferably comprises from 0.5% to 99%, preferably from 1% to 95%, more preferably from 5% to 90%, more preferably from 10% to 85%, even more preferably from 30% to 80% malted grain, most preferably from 30%-60% and even most preferably from 30%-50%. In addition to malted grain, the grist may preferably comprise adjunct such as unmalted maize, or other unmalted grain, such as barley, wheat, rye, oat, maize, rice, milo, millet and/or sorghum, or raw and/or refined starch and/or sugar containing material derived from plants like wheat, rye, oat, maize, rice, milo, millet, sorghum, potato, sweet potato, cassava, tapioca, sago, banana, sugar beet and/or sugar cane. The adjuncts may be obtained from tubers, roots, stems, leaves, legumes, cereals and/or whole grain. Preferred is adjunct obtained from maize and/or rice, more preferred the adjunct is maize. The mash preferably comprises from 1% to 80%, preferably from 5% to 80%, more preferably from 10% to 80%, and even more preferably from 30 to 80% adjunct starch, most preferably from 30-60% and even most preferably from 40-60%.

Preferably these adjuncts have high gelatinization temperature. More particularly, these adjuncts have a high onset gelatinization temperature.

In one aspect of the invention, the adjunct is a mixture comprising both high and low gelatinization temperature adjuncts.

When an aqueous solution of starch granules is heated, the granules swell to form a paste. This process is called "gelatinization". The temperature at which gelatinization occurs is called the "gelatinization temperature". Because of the complex nature of the starch in the adjuncts and also the conditions during mashing, the gelatinization actually occurs over a particular temperature range. The gelatinization temperature range thus can be characterised by the "onset gelatinization temperature", the "peak gelatinization temperature" and the "conclusion gelatinization temperature". For example, for corn starch, the onset gelatinization temperature is approximately 62° C. (peak: 67° C., conclusion: 72° C.), and for rice starch the onset gelatinization temperature is approximately 68° C. (peak: 74.5° C., conclusion: 78° C.) (Starch, 2nd ed. Industrial microscopy of starch by Eileen Maywald Snyder). The initial gelatinization temperature may vary according to the plant species, to the particular variety of the plant species as well as with the growth conditions.

Adjunct may also comprise readily fermentable carbohydrates such as sugars or syrups and they may be added to the malt mash before, during or after the mashing process of the invention but is preferably added after the mashing process.

Prior to forming the mash, the malt and/or adjunct is preferably milled and most preferably dry or wet milled.

The enzymes may be added as enzyme compositions. They may consist of one enzyme or more than one enzyme or more than one enzyme compositions. The enzyme composition, in addition to the enzyme(s), may also contain at least one other substance, for example but not limited to buffer, surfactants etc. The enzyme compositions may be in any art-recognized form, for example, solid, liquid, emulsion, gel, or paste. Such forms are known to the person skilled in the art. In one aspect of the invention more than one enzyme composition, each containing different enzymes may be added. In another aspect of the invention, one enzyme composition containing all the necessary enzymes may be added. In yet another aspect of the invention, one enzyme composition containing a few of the enzymes and at least one another composition containing some or all of the rest of the enzymes may be added In one aspect of the invention, an enzyme composition comprising an alpha amylase, a pullulanase, a maltogenic alpha amylase and/or a beta amylase is exogenously supplied and may be added to the mash ingredients, e.g. the water or the grist before during or after forming the mash, or at any time during the mashing.

During the mashing process, starch extracted from the grist is gradually hydrolyzed into fermentable sugars and smaller dextrins. Preferably the mash is starch negative to iodine testing, before extracting the wort. The mashing is finalized by mashing-off at temperature of 70° C. or more, preferably at least 71° C., at least 72° C., at least 73° C., at least 74° C., at least 75° C., at least 76° C. at least 77° C., at least 78° C., least 79° C., at least 80° C. and more preferably at least 81° C. or even at least 82° C. or more.

Obtaining the wort from the mash typically includes straining the wort from the spent grains, i.e. the insoluble grain and husk material forming part of grist. Hot water may be run through the spent grains to rinse out, or sparge, any remaining extract from the grist. Preferably, the extract recovery is at least 80%, preferably at least 85%, at least 90%. The wort may be used as it is, or it may be concentrated and/or dried.

The wort may also be processed to be used as syrups. It may also be used to produce non alcoholic beverages. These processes are known to a person skilled in the art.

The wort may also be fermented to beer. Preferred beer types comprise ales, strong ales, stouts, porters, lagers, bitters, export beers, malt liquors, happoushu, high-alcohol beer, low-alcohol beer, low-calorie beer or light beer. Fermentation of the wort may also include pitching the wort with a yeast slurry comprising fresh yeast, i.e. yeast not previously used for the invention or the yeast may be recycled yeast. The yeast applied may be any yeast suitable for beer brewing, especially yeasts selected from *Saccharomyces* spp. such as *S. cerevisiae* and *S. uvarum*, including natural or artificially produced variants of these organisms. The methods for fermentation of wort for production of beer are well known to the person skilled in the art. Silica hydrogel may be added to the fermented wort to increase the colloidal stability of the beer. The process may further include adding kieselguhr to the fermented wort and filtering to render the beer bright.

Enzymes

Maltogenic Alpha Amylase (EC 3.2.1.133)

The maltogenic alpha-amylase is an enzyme classified in EC 3.2.1.133. The enzymatic activity does not require a non-reducing end on the substrate and the primary enzymatic activity results in the degradation of amylopectin and amylose to maltose and longer maltodextrins. It is able to hydrolyze amylose and amylopectin to maltose in the alpha-configuration.

Examples of maltogenic amylases include but not limited to the amylase Novamyl® available from Novozymes A/S.

A particularly preferred maltogenic alpha-amylase is the maltogenic amylase of Seq ID No 1.

In one aspect of the invention the maltogenic alpha amylase has at least 70% identity, such as at least 75%, such as at least 80%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or even 100% identity to the sequence shown in SEQ ID No 1.

The term "identity" is the relatedness between two amino acid sequences or between two nucleotide sequences. For purposes of the present invention, the degree of identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends in Genetics 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

$$(\text{Identical Residues} \times 100)/(\text{Length of Alignment} - \text{Total Number of Gaps in Alignment})$$

In one aspect, the maltogenic alpha amylase has amino acid mutations at one or more specific positions in Seq ID. No 1. For example, the mutations may be at least at one or more positions Y89F, P191S, D261G, T288P, W93F, F194Y, Y360F or Y360 N. The nomenclature used herein for defining mutations is essentially as described in WO 92/05249. Thus, Y89F indicates a substitution of the amino acid Y (Tyr) in position 89 with the amino acid F (Phe). The methods for making these mutations are known to a person skilled in the art.

In one aspect the maltogenic alpha amylase has mutations at Y89F, P191S, D261G and T288P.

In another aspect, the maltogenic alpha amylase has additional mutations at least at W93F, F194Y, Y360F or Y360N.

In one aspect the maltogenic alpha amylase has mutations at Y89F, W93F, P191S, D261G and T288P.

In another aspect the maltogenic alpha amylase has mutations at Y89F, P191S, F194Y, D261G and T288P.

In one aspect the maltogenic alpha amylase has mutations at Y89F, P191S, D261G, T288P and Y360F.

In another aspect the maltogenic alpha amylase has mutations at Y89F, P191S, D261G, T288P and Y360N.

In one aspect, the maltogenic alpha amylase has at least 10% such as at least 15% such as at least 20% such as at least 25% or such as at least 30% or at least 35% or at least 40% or at least 45% or at least 50% or at least 55% or at least 60% or at least 65% or at least 70% or at least 75% more sucrose tolerance than the maltogenic alpha amylase of Seq ID No. 1.

The sucrose tolerance is determined using the method given in Example 5.

In one aspect, the maltogenic alpha amylase is thermostable.

In another aspect, the maltogenic alpha amylase has at least 10% or at least 15% or at least 20% or at least 25% or at least 30% or at least 35% or at least 40% or at least 45% or at least 50% or at least 55% or at least 60% or at least 65% or at least 70% or at least 75% more thermo stability than the maltogenic alpha amylase of Seq ID No. 1.

Thermostability of an enzyme is the capacity of the enzyme to resist irreversible thermal inactivation. For maltogenic amylase, it is determined by finding the amount of activity of the enzyme that remains after incubating the enzyme in a buffer (pH6) for 10 minutes both at 25° C. and at 72° C.

The maltogenic alpha amylase may be included in the range of 1-30, preferably 2-25, more preferably 5-20, or most preferably 8-13 MANU/g dry matter of the adjunct.

One Maltogenic Amylase Novo Unit (MANU) is the amount of enzyme which under standard will cleave one pmol maltotriose per minute. The standard conditions are 10 mg/ml maltotriose, 37° C., pH 5.0, 30 minutes reaction time.
Alpha-Amylase (EC 3.2.1.1)

An alpha-amylase enzyme may also be exogenous, microbial and added to the processes and/or compositions of the invention. The alpha-amylase may be a *Bacillus* alpha-amylase. Well-known *Bacillus* alpha-amylases include alpha-amylase derived from a strain of *B. licheniformis, B. amyloliquefaciens*, and *B. stearothermophilus*. A preferable alpha amylase is an alpha-amylase from *B. stearothermophilus* having the amino acid sequence disclosed as SEQ ID NO: 3 in WO 99/19467 with the mutations: I181*+G182*+N193F.

In one aspect, the alpha-amylase is an alpha amylase of Seq ID No.2.

In one aspect of the invention the alpha amylase has at least 70% identity, such as at least 75%, such as at least 80%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or even 100% identity to the sequence shown in SEQ ID No 2.

The alpha amylase may be added in the range of 0.001 to 10 KNU, preferably 0.01 to 5 KNU, even more preferably between 0.1 to 2 KNU per gram of dry matter of the adjunct.

One Kilo Novo alpha amylase Unit (KNU) equals 1000 NU. One KNU is defined as the amount of enzyme which, under standard conditions (i.e. at 37° C.+/−0.05; 0.0003 M Ca2+; and pH 5.6) dextrinizes 5.26 g starch dry substance Merck Amylum solubile.
Pullulanase (E.C. 3.2.1.41)

The pullulanases used in the processes according to the present invention is preferably pullulanase from e.g. *Pyrococcus* or *Bacillus* sp, such as *Bacillus acidopullulyticus* (e.g., the one described in FEMS Microbiol. Letters 115: 97-106) or *Bacillus deramificans*, or *Bacillus naganoencis*. The pullulanase may also be an engineered pullulanases from, e.g., a *Bacillus* strain.

Other pullulanases which is preferably used in the processes according to the invention includes: *Bacillus deramificans* (U.S. Pat. No. 5,736,375), or the pullulanase may be derived from *Pyrococcus Woesei* described in PCT/DK91/00219, or the pullulanase may be derived from *Fervidobacterium* sp. Ven 5 described in PCT/DK92/00079, or the pullulanase may be derived from *Thermococcus celer* described in PCT/DK95/00097, or the pullulanase may be derived from *Pyrodictium abyssei* described in PCT/DK95/00211, or the pullulanase may be derived from *Fervidobacterium pennavorans* described in PCT/DK95/00095, or the pullulanase may be derived from *Desulforococcus mucosus* described in PCT/DK95/00098.

Most preferably the pullulanase is derived from *Bacillus acidopullulyticus*.

A preferred pullulanase enzyme to be used in the processes and/or compositions of the invention is a pullulanase having an amino acid sequence of Seq ID No.3.

In one aspect of the invention the pullulanase has at least 70%, such as at least 75%, such as at least 80%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or even 100% identical to the sequence shown in Seq ID No: 3.

In one aspect of the invention, the pullulanase is thermostable. An example of such a pullulanase is a pullulanase described in WO2009075682.

For pullulanase, the thermostability is determined by finding the amount of activity of the enzyme that remains after incubating the enzyme in a buffer (pH 5) for 10 minutes both at 25° C. and at 64° C.

The pullulanase is added in dosage of 0.1 to 3 PUN/g dry matter (DM) adjunct, such as 0.2 to 2.9, such as 0.3 to 2.8, such as 0.3 to 2.7 such as 0.3 to 2.6 such as 0.3 to 2.5 such as 0.3 to 2.4, such as 0.3 to 2.3, such as 0.3 to 2.2, such as 0.3 to 2.1, such as 0.3 to 2.0, such as 0.3 to 1.9, such as 0.3 to 1.8, such as 0.3 to 1.7, such as 0.3 to 1.6, most preferably pullulanase is added in dosage such as 0.3 to 1.5, preferably 0.4 to 1.4, more preferably 0.5 to 1.3, more preferably 0.6 to 1.2, more preferably 0.7 to 1.1, more preferably 0.8 to 1.0, more preferably 0.9 to 1.0. In a particular embodiments of the invention the enzyme is added in 0.3 PUN/g DM adjunct, such as 0.4 PUN/g DM adjunct, such as 0.5 PUN/g DM adjunct, such as 0.6 PUN/g DM adjunct, such as 0.7 PUN/g DM adjunct. In a particularly preferred embodiment of the invention the enzymes dose is not larger than 1 PUN/g DM adjunct.

One pullulanase unit (PUN) is the amount of enzyme which, under standard conditions (i.e. after 30 minutes reaction time at 40° C. and pH 5.0; and with 0.2% pullulan as substrate) hydrolyzes pullulan, liberating reducing carbohydrate with a reducing power equivalent to 1 micromol glucose per minute.

Pullulanase activity is by measured by detection of increased reducing sugar capacity (Somogyi-Nelson reaction) in the following conditions: Substrate: 0.2% pullulan, pH 5.0, reaction time 30 minutes. The samples are analyzed by spectrophotometer at OD 520 nm.

Beta Amylase (E.C 3.2.1.2) Beta-amylase is the name traditionally given to exo-acting maltogenic amylases, which catalyze the hydrolysis of 1,4-alpha-glucosidic linkages in amylose, amylopectin and related glucose polymers.

Beta-amylases have been isolated from various plants and microorganisms (W. M. Fogarty and C. T. Kelly, 1979, Progress in Industrial Microbiology, 15: 112-115). These beta-amylases are characterized by having optimum temperatures in the range from 40 degree C. to 65.degree C. and optimum pH in the range from 4.5 to 7.0. Contemplated beta-amylases include the beta-amylase from barley Spezyme® BBA 1500, Spezyme® DBA and Optimalt™ ME, Optimalt™ BBA from Genencor Int. as well as Novozym™ WBA from Novozymes A/S.

Beta amylases are generally included in the range of 1 to 25 BAMU/g DM adjunct, such as from 1 to 20 BAMU/g DM adjunct, such as from 1 to 15 BAMU/g DM adjunct, such as from 1 to 10 BAMU/g DM adjunct, such as from 2 to 7 BAMU/g DM adjunct, such as from 2 to 6 BAMU/g DM adjunct, such as from 4 to 6 BAMU/g DM adjunct.

A beta-amylase unit (BAMU) is defined as the amount of enzyme that degrades one μmol maltohexaose per minute under the following conditions (37° C., pH 5.5, 200 sec incubation, 0.856 mM maltohexaose substrate, Sufficient activity of a maltose oxidizing enzyme releasing $H_2O_2$ e.g. 4.8 LOXU/mL lactose oxidase, 1.7 mM 4-aminoantipyrine (AA), 4.3 mM N-Ethyl-N-sulfopropyl-m-toluidine (TOPS), 2.1 U/mL peroxidise (Sigma).

Beta Amylase acts on the non-reducing end of maltohexaose (G6) to form maltose (G2) and maltotetraose (G4), the hydrolysis is measured with a method quantifying reducing end, such as the use of carbohydrate or lactose-oxidase and $O_2$ to form $H_2O_2$. The formed $H_2O_2$ activates in the presence of peroxidase the oxidative condensation of 4-aminoantipyrine (AA) and N-ethyl-N-sulfopropyl-m-toluidine (TOPS), to form a purple product which can be quantified by its absorbance at 540 nm. The reaction is initiated by maltohexaose (G6). When all components but beta amylase are in surplus, the rate of the rising absorbance is proportional to the beta amylase activity present.

In one aspect, the beta amylase is thermostable. An example of a thermostable beta amylase is the beta amylase from Clostridium thermosulfurogenes. An example of such a beta amylase is found in Kitamoto et al., 1988, J. Bacteriol, 170 (12) 5848-5854.

In one aspect, the beta amylase is a beta amylase having an amino acid sequence of Seq ID No 4.

In one aspect of the invention the beta amylase has at least 70% identity, such as at least 75%, such as at least 80%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or even 100% identity to the sequence shown in SEQ ID No 4.

EXAMPLES

Example 1

The objective of this example is to demonstrate the benefit of having all 3 enzymes (pullulanase, maltogenic alpha-amylase and an alpha amylase) present during mashing than only having 2 of them in different combinations and dosages.

A grist comprising 50% non-pre gelatinized maize grits and 50% well modified (WM) malt was ground (0.2 mm gap in a disc mill) and mashed in the presence of a pullulanase of Seq ID No. 3, an alpha-amylase of Seq ID No. 2, and a maltogenic alpha-amylase of Seq ID No.1. Maize and malt was mashed-in at a ratio of 1:5 (normal gravity) and the mashing temperature profile consisted of mashing-in at 52° C. for 30 min, increase to 62° C. (1° C./min), hold at 62° C. for 30 min, increase to 72° C. (1° C./min), hold at 72° C. for 30 min, increase to 78° C. (1° C./min) followed by immediate cooling to 20° C. (total mashing time of 131 minutes). The wort and fermented wort (one day lab. fermentation at room temperature) were analyzed by HPLC (sugar profile) and Anton Paar (% Real Degree of Fermentation, R D F and Extract, Ea). The following enzyme activities were dosed in all different combinations: 0 or 0.7 PUN pullulanase, 0 or 0.5 KNU alpha-amylase and 0 or 11.0 MANU maltogenic alpha-amylase per g Dry Matter adjunct.

All results are summarized in Table 1.

TABLE 1

| Units/g DM adjunct | % DP4+ (Δ%) | % RDF (Δ%) |
|---|---|---|
| No enzymes dosed (control) | 31.7 | 57.0 |
| 0.5 KNU | 28.6 (Δ 3.1) | 59.9 (Δ 2.9) |
| 0.5 KNU + 11 MANU | 22.2 (Δ 9.5) | 65.9 (Δ 8.9) |
| 0.5 KNU + 0.7 PUN | 26.7 (Δ 5.0) | 61.4 (Δ 4.4) |
| 11 MANU + 0.7 PUN | 21.2 (Δ 10.5) | 67.6 (Δ 10.6) |
| 0.5 KNU + 0.7 PUN + 11 MANU | 20.0 (Δ11.7) | 68.6 (Δ 11.6) |

The above data shows that the combination of an alpha amylase, a pullulanase and a maltogenic alpha amylase results in better wort characteristics than the use of the enzymes alone in single or in dual combinations.

Example 2

The objective was to assess the temperature optimum of beta-amylase from Clostridium thermosulfurogenes.

Temperature optimum of beta-amylase of Seq ID No. 4 obtainable from Clostridium thermosulfurogenes was determined by the release of maltose from amylopectin measuring the reducing ends by PHABH reagent. 1 mL substrate (1% w/v potato amylopectin in 50 mM NaOAc, 1 mM $CaCl_2$), pH 4.5) was pre-incubated at 60° C. for 10 minutes. As a control 150 μL was withdrawn prior to enzyme addition and mixed with 75 μL stop reagent (0.75 g PHABH (Sigma), 2.5 g K—Na-tartrate (Merck) and 50 ml 2% NaOH). For enzyme incubations, 150 μL enzyme solution was added to the substrate and incubated for 10 min at 30, 40, 50, 60, 70, or 80° C. 75 μL stop reagent was added and the solution was incubated at 100° C. for 15 min. 200 μL was transferred to PCR-tubes and absorbance measured at 410 nm. The experiment was carried out in triplicate. The pH optimum of beta-amylase from Clostridium thermosulfurogenes was determined according to the above procedure with the following modifications. Incubation was carried out at 60° C. at pH 4, 5, 6, 7, 8 or 9.

TABLE 2

| Temperature optimum | |
|---|---|
| ° C. | Abs410 |
| 30 | 0.255 |
| 40 | 0.325 |
| 50 | 0.329 |
| 60 | 0.414 |
| 70 | 0.470 |
| 80 | 0.471 |

TABLE 3 pH optimum

| pH | Abs410 |
|---|---|
| 4 | 0.402 |
| 5 | 0.524 |
| 6 | 0.631 |
| 7 | 0.595 |
| 8 | 0.354 |
| 9 | 0.140 |

The beta-amylase from *Clostridium thermosulfurogenes* has temperature optimum at 70-80° C. and pH optimum around pH 5-7 (Table 2 and 3). In comparison, barley beta-amylase has temperature optimum at 60-65° C. at mash conditions (pH 5.8) (Kunze (1999), Technology Brewing and Malting, VLB Verlag, Berlin).

Example 3

The objective of this example was to demonstrate the benefit of having a thermostable beta-amylase present during mashing and lautering in combination with a pullulanase and alpha-amylase.

A grist comprising 50% non-pre gelatinized maize grits and 50% well modified (WM) malt was grinded (0.2 mm gap in a disc mill) was mashed in the presence of a pullulanase of Seq ID No.3, a alpha-amylase of Seq ID No 2 and beta amylase of Seq ID No. 4. Maize and malt was mashed-in at a ratio of 1:5 (normal gravity) and the mashing temperature profile consisted of mashin-in at 52° C. for 30 min, increase to 62° C. (1° C./min), hold at 62° C. for 30 min, increase to 72° C. (1° C./min), hold at 72° C. for 30 min, increase to 78° C. (1° C./min) followed by incubation for 2 hours at 78° C. (simulated lautering) followed by immediate cooling to 20° C. The wort and fermented wort (one day lab fermentation at room temperature) were analyzed by HPLC (sugar profile) and Anton Paar (% Real Degree of Fermentation, R D F and Extract, Ea). The following enzyme activities were dosed in all different combinations: 0 or 0.7 PUN pullulanase, 0, 0.15 KNU alpha-amylase and 0 or 2.5 BAMU beta-amylase per g Dry Matter adjunct. The results are given in Table 4 below:

TABLE 4

Wort sugar profile (% of total sugars) and % RDF (Real Degree of Fermentation) in the fermented wort. Pullulanase (PUN), alpha-amylase (KNU), beta-amylase (BAMU).

| Enzyme dosage (Units/g DM adjunct) | | | | |
|---|---|---|---|---|
| PUN | KNU | BAMU | % DP4+ | % RDF |
| — | — | — | 26.6 | 57.4 |
| 0.7 | — | — | 23.3 | 60.0 |
| 0.7 | 0.15 | — | 20.8 | 62.6 |
| 0.7 | 0.15 | 2.5 | 14.2 | 69.8 |

Table 4 demonstrates the benefit of having a thermostable beta-amylase present during mashing in combination with a pullulanase and alpha-amylase. A markedly higher level of maltose was obtained resulting in a lower level of non-fermentable sugars (DP4+) and correspondingly a higher % RDF of the fermented wort.

Example 4

A grist comprising 50% non-pre gelatinized maize grits and 50% well modified (WM) malt was grinded (0.2 mm gap in a disc mill) and mashed in the presence of a maltogenic alpha-amylase of Seq ID No. 1, an alpha-amylase of Seq ID No. 2, and a Pullulanase of Seq ID No.3. Maize and malt was mashed-in at a ratio of 1:3 (high gravity) and the mashing temperature profile consisted of mashing-in at 52° C. for 30 min, increase to 62° C. (1° C./min), hold at 62° C. for 30 min, increase to 72° C. (1° C./min), hold at 72° C. for 30 min, increase to 78° C. (1° C./min) and then immediately cooling to 20° C. (3.9° C./min) resulting in a total mashing time of 131 minutes. The wort and fermented wort (one day lab fermentation at room temperature) were analyzed by HPLC (sugar profile) and Anton Paar (% Real Degree of Fermentation, R D F and Extract, Ea). The following enzyme activities were dosed: 0.7 PUN pullulanase, 0.5 KNU alpha-amylase and 11.0 MANU maltogenic alpha-amylase per gram of dry matter adjunct.

Results are summarized in Table 5, demonstrating that the combination of a maltogenic amylase, an alpha amylase and a pullulanase results in improvement in starch hydrolysis, maltose formation and % RDF.

TABLE 5

Enzyme dosage, wort sugar profile (% of total sugar), wort extract level (g/100 mL) and % RDF obtained for the 4 enzyme variants in comparison to the wild type.

| Maltogenic alpha-amylase | % DP1 | % DP2 | % DP3 | % DP4+ | Extract (g/100 mL) | % RDF |
|---|---|---|---|---|---|---|
| Seq ID No 1 | 16.7 | 42.1 | 14.8 | 25.1 | 20.6 | 65.4 |
| Variant 1 | 18.7 | 43.6 | 13.4 | 23.3 | 20.6 | 70.3 |
| Variant 2 | 20.6 | 45.3 | 13.5 | 19.4 | 20.6 | 69.8 |
| Variant 3 | 18.4 | 43.5 | 14.0 | 22.9 | 20.7 | 67.1 |
| Variant 4 | 18.3 | 43.3 | 14.3 | 22.9 | 20.6 | 67.4 |

The variants are defined in example 5, table 6 below.

The terms "DP1" (Degree of polymerization 1) denotes glucose, "DP2" denotes maltose and DP3 denotes maltotriose. The terms "DP4+" or "DP4/4+" denote dextrin, or maltooligosaccharides of a polymerization degree of 4 or higher.

The term "RDF" means real degree of fermentation. RDF (Real degree of fermentation) is calculated as % RDF=100* (OE % P–ER %)/OE % P whereas OE means Original Extract in % P and ER means Real Extract % P measured by a densitometer (Analytica EBC reference). RDF: Real Degree of Fermentation, was determined by the method described in MEBAK method: 2.9.2.

Principal: Reduction of wort dry matter, in %, by fermentation to alcohol and CO2.

The table above demonstrates that the variants give a higher RDF than the enzyme of Seq ID No 1. Among the variants, variant 2 appears to be the best.

Example 5

Sucrose tolerance of 4 maltogenic alpha-amylase variants was studied.

Sucrose tolerance was determined by incubating the given enzyme in a buffer (pH 5.0) containing 10% sucrose (% w/v) for 15 minutes at 60° C. Immediately after incubation the residual activity of the enzyme was determined by the Phadebas assay (endo alpha-amylase activity). 100% sucrose tolerance corresponds to the residual activity obtained of the maltogenic alpha-amylase when no sucrose is present in the incubation buffer.

Results are summarized in Table 6 demonstrating that the 4 maltogenic alpha-amylase variants are more sucrose tolerant than the wild type.

TABLE 6

Amino acid modifications and sucrose tolerance of maltogenic alpha-amylase enzyme variants in comparison to the wild type.

| Maltogenic alpha-amylase | Amino acid modifications | % sucrose tolerance. |
| --- | --- | --- |
| Seq ID No 1. | — | 12 |
| Variant 1 | Y89F, W93F, P191S, D261G, T288P | 70 |

TABLE 6-continued

Amino acid modifications and sucrose tolerance of maltogenic alpha-amylase enzyme variants in comparison to the wild type.

| Maltogenic alpha-amylase | Amino acid modifications | % sucrose tolerance. |
| --- | --- | --- |
| Variant 2 | Y89F, P191S, F194Y, D261G, T288P | 53 |
| Variant 3 | Y89F, P191S, D261G, T288P, Y360F | 40 |
| Variant 4 | Y89F, P191S, D261G, T288P, Y360N | 40 |

From the table, it is apparent that variant 1 is 58%, variant 2 is 41% and variant 3 and 4 are 28% more sucrose tolerant that Seq ID No.1 respectively.

The invention claimed is:

1. A method of mashing comprising:
   a) providing a grist comprising malt and adjunct, wherein the grist comprises 40-60% adjunct, wherein the adjunct has a gelatinization temperature higher than the malt starch, and wherein the adjunct is not gelatinized prior to mashing; and
   b) contacting the grist with the following combination of the enzymes, consisting of:
      i) a pullulanase;
      ii) an alpha amylase; and
      iii) a maltogenic alpha amylase, wherein the maltogenic alpha amylase is at least 10% more sucrose tolerant than a maltogenic alpha amylase comprising SEQ ID NO: 1, wherein the sucrose tolerance is measured in a buffer containing 10% sucrose (% w/v) at pH 5.0 for 15 minutes at 60° C. in accordance with example 5, to make a wort.

2. The method according to claim 1, wherein the adjunct is maize or rice.

3. The method according to claim 1, wherein the maltogenic alpha amylase has at least 70% identity to SEQ ID NO: 1.

4. The method according to claim 1, wherein the alpha amylase has at least 70% identity to SEQ ID NO: 2.

5. The method according to claim 1, wherein the pullulanase has at least 70% identity to SEQ ID NO: 3.

6. The method according to claim 1, wherein the pullulanase is thermostable wherein the thermostability is measured by finding the amount of activity of the enzyme that remains after incubating the enzyme in a buffer at pH 5.0 for 10 minutes both at 25° C. and at 64° C.

7. The method according to claim 3, wherein the maltogenic alpha amylase comprises the substitutions at positions Y89F, P191S, D261G and T288P in SEQ ID NO: 1.

8. The method according to claim 3, wherein the maltogenic alpha amylase comprises one or more of the substitutions W93F, Y360F, Y360N and F194Y in SEQ ID NO: 1.

9. The method according to claim 1, wherein the wort is converted to beer.

10. The method according to claim 1, further comprising contacting the grist with a beta amylase.

11. The method according to claim 10, wherein the beta amylase has at least 70% identity to SEQ ID NO: 4.

12. The method according to claim 10, wherein the beta amylase has a temperature optimum of 70-80° C. wherein the temperature optimum is measured in accordance to example 2.

* * * * *

SEQUENCE LISTING

<160> NUMBER OF SEQ ID NOS: 4

<210> SEQ ID NO 1
<211> LENGTH: 685
<212> TYPE: PRT
<213> ORGANISM: Bacillus stearothermophilus

<400> SEQUENCE: 1

```
Ala Ser Ser Ser Ala Ser Val Lys Gly Asp Val Ile Tyr Gln Ile Ile
1               5                   10                  15

Ile Asp Arg Phe Tyr Asp Gly Asp Thr Thr Asn Asn Asn Pro Ala Lys
            20                  25                  30

Ser Tyr Gly Leu Tyr Asp Pro Thr Lys Ser Lys Trp Lys Met Tyr Trp
        35                  40                  45

Gly Gly Asp Leu Glu Gly Val Arg Gln Lys Leu Pro Tyr Leu Lys Gln
    50                  55                  60

Leu Gly Val Thr Thr Ile Trp Leu Ser Pro Val Leu Asn Asn Leu Asp
65                  70                  75                  80

Thr Leu Ala Gly Thr Asp Asn Thr Gly Tyr His Gly Tyr Trp Thr Arg
                85                  90                  95

Asp Phe Lys Gln Ile Glu Glu His Phe Gly Asn Trp Thr Thr Phe Asp
            100                 105                 110

Thr Leu Val Asn Asp Ala His Gln Asn Gly Ile Lys Val Ile Val Asp
        115                 120                 125

Phe Val Pro Asn His Ser Thr Pro Phe Lys Ala Asn Asp Ser Thr Phe
    130                 135                 140

Ala Glu Gly Gly Ala Leu Tyr Asn Asn Gly Thr Tyr Met Gly Asn Tyr
145                 150                 155                 160

Phe Asp Asp Ala Thr Lys Gly Tyr Phe His His Asn Gly Asp Ile Ser
                165                 170                 175

Asn Trp Asp Asp Arg Tyr Glu Ala Gln Trp Lys Asn Phe Thr Asp Pro
            180                 185                 190

Ala Gly Phe Ser Leu Ala Asp Leu Ser Gln Glu Asn Gly Thr Ile Ala
        195                 200                 205

Gln Tyr Leu Thr Asp Ala Ala Val Gln Leu Val Ala His Gly Leu Arg
    210                 215                 220

Ile Asp Ala Val Lys His Phe Asn Ser Gly Phe Ser Lys Ser Leu Ala
225                 230                 235                 240

Asp Lys Leu Tyr Gln Lys Lys Asp Ile Phe Leu Val Gly Glu Trp Tyr
                245                 250                 255

Gly Asp Asp Pro Gly Thr Ala Asn His Leu Glu Lys Val Arg Tyr Ala
            260                 265                 270
```

```
Asn Asn Ser Gly Val Asn Val Leu Asp Phe Asp Leu Asn Thr Val Ile
            275                 280                 285

Arg Asn Val Phe Gly Thr Phe Thr Gln Thr Met Tyr Asp Leu Asn Asn
290                 295                 300

Met Val Asn Gln Thr Gly Asn Glu Tyr Lys Tyr Lys Glu Asn Leu Ile
305                 310                 315                 320

Thr Phe Ile Asp Asn His Asp Met Ser Arg Phe Leu Ser Val Asn Ser
            325                 330                 335

Lys Asn Lys Ala Asn Leu His Gln Arg Leu Leu Ser Phe Ser Leu Arg
            340                 345                 350

Gly Val Arg Pro Pro Ile Tyr Tyr Gly Thr Glu Gln Tyr Met Ala Gly
            355                 360                 365

Gly Asn Asp Pro Tyr Asn Arg Gly Met Met Pro Ala Phe Asp Thr Thr
            370                 375                 380

Thr Thr Ala Phe Lys Glu Val Ser Thr Leu Ala Gly Leu Arg Arg Asn
385                 390                 395                 400

Asn Ala Ala Ile Gln Tyr Gly Thr Thr Thr Gln Arg Trp Ile Asn Asn
                405                 410                 415

Asp Val Tyr Ile Tyr Glu Arg Lys Phe Phe Asn Asp Val Val Leu Val
                420                 425                 430

Ala Ile Asn Arg Asn Thr Gln Ser Ser Tyr Ser Ile Ser Gly Leu Gln
                435                 440                 445

Thr Ala Leu Pro Asn Gly Ser Tyr Ala Asp Tyr Leu Ser Gly Leu Leu
            450                 455                 460

Gly Gly Asn Gly Ile Ser Val Ser Asn Gly Ser Val Ala Ser Phe Thr
465                 470                 475                 480

Leu Ala Pro Gly Ala Val Ser Val Trp Gln Tyr Ser Thr Ser Ala Ser
                485                 490                 495

Ala Pro Gln Ile Gly Ser Val Ala Pro Asn Met Gly Ile Pro Gly Asn
                500                 505                 510

Val Val Thr Ile Asp Gly Lys Gly Phe Gly Thr Thr Gln Gly Thr Val
                515                 520                 525

Thr Phe Gly Gly Val Thr Ala Thr Val Lys Ser Trp Thr Ser Asn Arg
            530                 535                 540

Ile Glu Val Tyr Val Pro Asn Met Ala Ala Gly Leu Thr Asp Val Lys
545                 550                 555                 560

Val Thr Ala Gly Gly Val Ser Ser Asn Leu Tyr Ser Tyr Asn Ile Leu
                565                 570                 575

Ser Gly Thr Gln Thr Ser Val Val Phe Thr Val Lys Ser Ala Pro Pro
            580                 585                 590

Thr Asn Leu Gly Asp Lys Ile Tyr Leu Thr Gly Asn Ile Pro Glu Leu
            595                 600                 605

Gly Asn Trp Ser Thr Asp Thr Ser Gly Ala Val Asn Asn Ala Gln Gly
            610                 615                 620

Pro Leu Leu Ala Pro Asn Tyr Pro Asp Trp Phe Tyr Val Phe Ser Val
625                 630                 635                 640

Pro Ala Gly Lys Thr Ile Gln Phe Lys Phe Ile Lys Arg Ala Asp
                645                 650                 655

Gly Thr Ile Gln Trp Glu Asn Gly Ser Asn His Val Ala Thr Thr Pro
            660                 665                 670

Thr Gly Ala Thr Gly Asn Ile Thr Val Thr Trp Gln Asn
            675                 680                 685
```

```
<210> SEQ ID NO 2
<211> LENGTH: 491
<212> TYPE: PRT
<213> ORGANISM: Bacillus stearothermophilus

<400> SEQUENCE: 2

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Lys Ala Trp Asp Trp Glu Val Asp Thr Glu Phe Gly
            180                 185                 190

Asn Tyr Asp Tyr Leu Met Tyr Ala Asp Leu Asp Met Asp His Pro Glu
        195                 200                 205

Val Val Thr Glu Leu Lys Asn Trp Gly Lys Trp Tyr Val Asn Thr Thr
    210                 215                 220

Asn Ile Asp Gly Phe Arg Leu Asp Ala Val Lys His Ile Lys Phe Ser
225                 230                 235                 240

Phe Phe Pro Asp Trp Leu Ser Tyr Val Arg Ser Gln Thr Gly Lys Pro
                245                 250                 255

Leu Phe Thr Val Gly Glu Tyr Trp Ser Tyr Asp Ile Asn Lys Leu His
            260                 265                 270

Asn Tyr Ile Thr Lys Thr Asn Gly Thr Met Ser Leu Phe Asp Ala Pro
        275                 280                 285

Leu His Asn Lys Phe Tyr Thr Ala Ser Lys Ser Gly Gly Ala Phe Asp
    290                 295                 300

Met Arg Thr Leu Met Thr Asn Thr Leu Met Lys Asp Gln Pro Thr Leu
305                 310                 315                 320

Ala Val Thr Phe Val Asp Asn His Asp Thr Glu Pro Gly Gln Ala Leu
                325                 330                 335

Gln Ser Trp Val Asp Pro Trp Phe Lys Pro Leu Ala Tyr Ala Phe Ile
            340                 345                 350

Leu Thr Arg Gln Glu Gly Tyr Pro Cys Val Phe Tyr Gly Asp Tyr Tyr
        355                 360                 365

Gly Ile Pro Gln Tyr Asn Ile Pro Ser Leu Lys Ser Lys Ile Asp Pro
    370                 375                 380
```

-continued

```
Leu Leu Ile Ala Arg Arg Asp Tyr Ala Tyr Gly Thr Gln His Asp Tyr
385                 390                 395                 400

Leu Asp His Ser Asp Ile Ile Gly Trp Thr Arg Glu Gly Val Thr Glu
            405                 410                 415

Lys Pro Gly Ser Gly Leu Ala Ala Leu Ile Thr Asp Gly Pro Gly Gly
            420                 425                 430

Ser Lys Trp Met Tyr Val Gly Lys Gln His Ala Gly Lys Val Phe Tyr
            435                 440                 445

Asp Leu Thr Gly Asn Arg Ser Asp Thr Val Thr Ile Asn Ser Asp Gly
    450                 455                 460

Trp Gly Glu Phe Lys Val Asn Gly Gly Ser Val Ser Val Trp Val Pro
465                 470                 475                 480

Arg Lys Thr Thr Val Ser Thr Ile Ala Arg Pro
            485                 490
```

<210> SEQ ID NO 3
<211> LENGTH: 829
<212> TYPE: PRT
<213> ORGANISM: Bacillus acidopullulyticus

<400> SEQUENCE: 3

```
Asp Ser Thr Ser Thr Glu Val Ile Val His Tyr His Arg Phe Asp Ser
1               5                   10                  15

Asn Tyr Ala Asn Trp Asp Leu Trp Met Trp Pro Tyr Gln Pro Val Asn
            20                  25                  30

Gly Asn Gly Ala Ala Tyr Glu Phe Ser Gly Lys Asp Asp Phe Gly Val
        35                  40                  45

Lys Ala Asp Val Gln Val Pro Gly Asp Asp Thr Gln Val Gly Leu Ile
50                  55                  60

Val Arg Thr Asn Asp Trp Ser Gln Lys Asn Thr Ser Asp Asp Leu His
65                  70                  75                  80

Ile Asp Leu Thr Lys Gly His Glu Ile Trp Ile Val Gln Gly Asp Pro
                85                  90                  95

Asn Ile Tyr Tyr Asn Leu Ser Asp Ala Gln Ala Ala Thr Pro Lys
            100                 105                 110

Val Ser Asn Ala Tyr Leu Asp Asn Glu Lys Thr Val Leu Ala Lys Leu
        115                 120                 125

Thr Asn Pro Met Thr Leu Ser Asp Gly Ser Ser Gly Phe Thr Val Thr
    130                 135                 140

Asp Lys Thr Thr Gly Glu Gln Ile Pro Val Thr Ala Ala Thr Asn Ala
145                 150                 155                 160

Asn Ser Ala Ser Ser Ser Glu Gln Thr Asp Leu Val Gln Leu Thr Leu
                165                 170                 175

Ala Ser Ala Pro Asp Val Ser His Thr Ile Gln Val Gly Ala Ala Gly
            180                 185                 190

Tyr Glu Ala Val Asn Leu Ile Pro Arg Asn Val Leu Asn Leu Pro Arg
        195                 200                 205

Tyr Tyr Tyr Ser Gly Asn Asp Leu Gly Asn Val Tyr Ser Asn Lys Ala
    210                 215                 220

Thr Ala Phe Arg Val Trp Ala Pro Thr Ala Ser Asp Val Gln Leu Leu
225                 230                 235                 240

Leu Tyr Asn Ser Glu Thr Gly Pro Val Thr Lys Gln Leu Glu Met Gln
                245                 250                 255

Lys Ser Asp Asn Gly Thr Trp Lys Leu Lys Val Pro Gly Asn Leu Lys
            260                 265                 270
```

```
Asn Trp Tyr Tyr Leu Tyr Gln Val Thr Val Asn Gly Lys Thr Gln Thr
            275                 280                 285

Ala Val Asp Pro Tyr Val Arg Ala Ile Ser Val Asn Ala Thr Arg Gly
        290                 295                 300

Met Ile Val Asp Leu Glu Asp Thr Asn Pro Pro Gly Trp Lys Glu Asp
305                 310                 315                 320

His Gln Gln Thr Pro Ala Asn Pro Val Asp Glu Val Ile Tyr Glu Val
                325                 330                 335

His Val Arg Asp Phe Ser Ile Asp Ala Asn Ser Gly Met Lys Asn Lys
            340                 345                 350

Gly Lys Tyr Leu Ala Phe Thr Glu His Gly Thr Lys Gly Pro Asp Asn
        355                 360                 365

Val Lys Thr Gly Ile Asp Ser Leu Lys Glu Leu Gly Ile Asn Ala Val
    370                 375                 380

Gln Leu Gln Pro Ile Glu Glu Phe Asn Ser Ile Asp Glu Thr Gln Pro
385                 390                 395                 400

Asn Met Tyr Asn Trp Gly Tyr Asp Pro Arg Asn Tyr Asn Val Pro Glu
                405                 410                 415

Gly Ala Tyr Ala Thr Thr Pro Glu Gly Thr Ala Arg Ile Thr Gln Leu
            420                 425                 430

Lys Gln Leu Ile Gln Ser Ile His Lys Asp Arg Ile Ala Ile Asn Met
        435                 440                 445

Asp Val Val Tyr Asn His Thr Phe Asn Val Gly Val Ser Asp Phe Asp
    450                 455                 460

Lys Ile Val Pro Gln Tyr Tyr Tyr Arg Thr Asp Ser Ala Gly Asn Tyr
465                 470                 475                 480

Thr Asn Gly Ser Gly Val Gly Asn Glu Ile Ala Thr Glu Arg Pro Met
                485                 490                 495

Val Gln Lys Phe Val Leu Asp Ser Val Lys Tyr Trp Val Lys Glu Tyr
            500                 505                 510

His Ile Asp Gly Phe Arg Phe Asp Leu Met Ala Leu Leu Gly Lys Asp
        515                 520                 525

Thr Met Ala Lys Ile Ser Lys Glu Leu His Ala Ile Asn Pro Gly Ile
    530                 535                 540

Val Leu Tyr Gly Glu Pro Trp Thr Gly Gly Thr Ser Gly Leu Ser Ser
545                 550                 555                 560

Asp Gln Leu Val Thr Lys Gly Gln Gln Lys Gly Leu Gly Ile Gly Val
                565                 570                 575

Phe Asn Asp Asn Ile Arg Asn Gly Leu Asp Gly Asn Val Phe Asp Lys
            580                 585                 590

Ser Ala Gln Gly Phe Ala Thr Gly Asp Pro Asn Gln Val Asn Val Ile
        595                 600                 605

Lys Asn Gly Val Met Gly Ser Ile Ser Asp Phe Thr Ser Ala Pro Ser
    610                 615                 620

Glu Thr Ile Asn Tyr Val Thr Ser His Asp Asn Met Thr Leu Trp Asp
625                 630                 635                 640

Lys Ile Ser Ala Ser Asn Pro Asn Asp Thr Gln Ala Asp Arg Ile Lys
                645                 650                 655

Met Asp Glu Leu Ala Gln Ala Val Val Phe Thr Ser Gln Gly Val Pro
            660                 665                 670

Phe Met Gln Gly Gly Glu Glu Met Leu Arg Thr Lys Gly Gly Asn Asp
        675                 680                 685
```

```
Asn Ser Tyr Asn Ala Gly Asp Ser Val Asn Gln Phe Asp Trp Ser Arg
    690                 695                 700
Lys Ala Gln Phe Glu Asn Val Phe Asp Tyr Tyr Ser Trp Leu Ile His
705                 710                 715                 720
Leu Arg Asp Asn His Pro Ala Phe Arg Met Thr Thr Ala Asp Gln Ile
                725                 730                 735
Lys Gln Asn Leu Thr Phe Leu Asp Ser Pro Thr Asn Thr Val Ala Phe
            740                 745                 750
Glu Leu Lys Asn His Ala Asn His Asp Lys Trp Lys Asn Ile Ile Val
        755                 760                 765
Met Tyr Asn Pro Asn Lys Thr Ala Gln Thr Leu Thr Leu Pro Ser Gly
770                 775                 780
Asn Trp Thr Ile Val Gly Leu Gly Asn Gln Val Gly Glu Lys Ser Leu
785                 790                 795                 800
Gly His Val Asn Gly Thr Val Glu Val Pro Ala Leu Ser Thr Ile Ile
                805                 810                 815
Leu His Gln Gly Thr Ser Glu Asp Val Ile Asp Gln Asn
            820                 825

<210> SEQ ID NO 4
<211> LENGTH: 551
<212> TYPE: PRT
<213> ORGANISM: Clostridium thermasulforogenes

<400> SEQUENCE: 4

Met Ile Gly Ala Phe Lys Arg Leu Gly Gln Lys Leu Phe Leu Thr Leu
1               5                   10                  15
Leu Thr Ala Ser Leu Ile Phe Ala Ser Ser Ile Val Thr Ala Asn Ala
            20                  25                  30
Ser Ile Ala Pro Asn Phe Lys Val Phe Val Met Gly Pro Leu Glu Lys
        35                  40                  45
Val Thr Asp Phe Asn Ala Phe Lys Asp Gln Leu Ile Thr Leu Lys Asn
    50                  55                  60
Asn Gly Val Tyr Gly Ile Thr Thr Asp Ile Trp Trp Gly Tyr Val Glu
65              70                  75                  80
Asn Ala Gly Glu Asn Gln Phe Asp Trp Ser Tyr Tyr Lys Thr Tyr Ala
                85                  90                  95
Asp Thr Val Arg Ala Ala Gly Leu Lys Trp Val Pro Ile Met Ser Thr
            100                 105                 110
His Ala Cys Gly Gly Asn Val Gly Asp Thr Val Asn Ile Pro Ile Pro
        115                 120                 125
Ser Trp Val Trp Thr Lys Asp Thr Gln Asp Asn Met Gln Tyr Lys Asp
    130                 135                 140
Glu Ala Gly Asn Trp Asp Asn Glu Ala Val Ser Pro Trp Tyr Ser Gly
145                 150                 155                 160
Leu Thr Gln Leu Tyr Asn Glu Phe Tyr Ser Ser Phe Ala Ser Asn Phe
                165                 170                 175
Ser Ser Tyr Lys Asp Ile Ile Thr Lys Ile Tyr Ile Ser Gly Gly Pro
            180                 185                 190
Ser Gly Glu Leu Arg Tyr Pro Ser Tyr Asn Pro Ser His Gly Trp Thr
        195                 200                 205
Tyr Pro Gly Arg Gly Ser Leu Gln Cys Tyr Ser Lys Ala Ala Ile Thr
    210                 215                 220
Ser Phe Gln Asn Ala Met Lys Ser Lys Tyr Gly Thr Ile Ala Ala Val
225                 230                 235                 240
```

```
Asn Ser Ala Trp Gly Thr Ser Leu Thr Asp Phe Ser Gln Ile Ser Pro
            245                 250                 255

Pro Thr Asp Gly Asp Asn Phe Phe Thr Asn Gly Tyr Lys Thr Thr Tyr
            260                 265                 270

Gly Asn Asp Phe Leu Thr Trp Tyr Gln Ser Val Leu Thr Asn Glu Leu
            275                 280                 285

Ala Asn Ile Ala Ser Val Ala His Ser Cys Phe Asp Pro Val Phe Asn
            290                 295                 300

Val Pro Ile Gly Ala Lys Ile Ala Gly Val His Trp Leu Tyr Asn Ser
305                     310                 315                 320

Pro Thr Met Pro His Ala Ala Glu Tyr Cys Ala Gly Tyr Tyr Asn Tyr
            325                 330                 335

Ser Thr Leu Leu Asp Gln Phe Lys Ala Ser Asn Leu Ala Met Thr Phe
            340                 345                 350

Thr Cys Leu Glu Met Asp Asp Ser Asn Ala Tyr Val Ser Pro Tyr Tyr
            355                 360                 365

Ser Ala Pro Met Thr Leu Val His Tyr Val Ala Asn Leu Ala Asn Asn
            370                 375                 380

Lys Gly Ile Val His Asn Gly Glu Asn Ala Leu Ala Ile Ser Asn Asn
385                     390                 395                 400

Asn Gln Ala Tyr Val Asn Cys Ala Asn Glu Leu Thr Gly Tyr Asn Phe
            405                 410                 415

Ser Gly Phe Thr Leu Leu Arg Leu Ser Asn Ile Val Asn Ser Asp Gly
            420                 425                 430

Ser Val Thr Ser Glu Met Ala Pro Phe Val Ile Asn Ile Val Thr Leu
            435                 440                 445

Thr Pro Asn Gly Thr Ile Pro Val Thr Phe Thr Ile Asn Asn Ala Thr
450                     455                 460

Thr Tyr Tyr Gly Gln Asn Val Tyr Ile Val Gly Ser Thr Ser Asp Leu
465                     470                 475                 480

Gly Asn Trp Asn Thr Thr Tyr Ala Arg Gly Pro Ala Ser Cys Pro Asn
                485                 490                 495

Tyr Pro Thr Trp Thr Ile Thr Leu Asn Leu Leu Pro Gly Glu Gln Ile
            500                 505                 510

Gln Phe Lys Ala Val Lys Ile Asp Ser Ser Gly Asn Val Thr Trp Glu
            515                 520                 525

Gly Gly Ser Asn His Thr Tyr Thr Val Pro Thr Ser Gly Thr Gly Ser
            530                 535                 540

Val Thr Ile Thr Trp Gln Asn
545                 550
```